United States Patent [19]

Summers et al.

[11] 4,210,609

[45] Jul. 1, 1980

[54] METHOD OF TREATING 1-NITROPROPANE

[75] Inventors: William A. Summers, Terre Haute, Ind.; Peter C. Markunas, Springfield, Ill.; Lois V. Faulkner, Daly City, Calif.

[73] Assignee: International Minerals & Chemical Corp., Terre Haute, Ind.

[21] Appl. No.: 936,315

[22] Filed: Aug. 23, 1978

[51] Int. Cl.$^2$ .............................................. C07C 79/04
[52] U.S. Cl. ..................................... 568/947; 260/708
[58] Field of Search ................................. 260/644, 708

[56] References Cited

U.S. PATENT DOCUMENTS

| 3,657,364 | 4/1972 | Crawford et al. | 260/644 |
| 3,706,808 | 12/1972 | Bachman et al. | 260/644 |

FOREIGN PATENT DOCUMENTS

| 4622004 | 12/1968 | Japan | 260/644 |

*Primary Examiner*—Leland A. Sebastian
*Attorney, Agent, or Firm*—Robert H. Dewey

[57] ABSTRACT

A process for decolorizing 1-nitropropane containing color bodies by passing it through a bed of alumina.

5 Claims, No Drawings

METHOD OF TREATING 1-NITROPROPANE

BACKGROUND OF THE INVENTION

This invention relates to a method of treating 1-nitropropane. In a particular aspect, this invention relates to a method of treating 1-nitropropane to remove color bodies and stabilize it against further color development.

1-Nitropropane is obtained commercially by the vapor phase nitration of propane, which also yields nitromethane, nitroethane and 2-nitropropane. These latter three products are relatively stable during storage, when dry, but 1-nitropropane has always suffered from color development during storage. The identity of the color bodies responsible for color development has never been established. Similarly, it has never been established as to the mechanism of the formation of these color bodies. That is, it is not known whether the color bodies are formed during the nitration process, during the recovery and purification steps, or are formed as a result of storage conditions. In any case, the color has been difficult to remove. This property has tended to hinder its commercial usage, although it has excellent solvent properties in a variety of applications.

SUMMARY OF THE INVENTION

It is an object of this invention to provide a method of treating 1-nitropropane.

It is another object of this invention to provide a method of removing color bodies from 1-nitropropane.

It is yet another object of this invention to provide a method of stabilizing 1-nitropropane against color development during storage.

Other objects of this invention will be apparent to those skilled in the art.

It is the discovery of this invention to remove color bodies from 1-nitropropane and to stabilize against color development during storage by treating it with activated alumina by passing it through a bed of alumina. After the alumina is exhausted, retained 1-nitropropane is recovered.

DETAILED DISCUSSION

The 1-nitropropane (1-NP) for which the process of this invention is intended is preferably commercial grade material, i.e. it is material which has been subjected to the usual rectification procedures, including fractional distillation. Generally, but not necessarily, the 1-NP will have been in storage and will have developed color beyond that of "water-white", which is the specification limit. "Water-white" is customarily interpreted to mean 20 on the scale adopted by the American Public Health Association (APHA) and that is the meaning intended herein. A color of 90 APHA or more is typical of 1-NP except when freshly distilled. The ratio of 1-NP to alumina depends somewhat on the degree of color. Also, the capacity of the alumina is directly proportional to the pressure and—to a limited extent—the space velocity. The latter function appears to be parabolic. In any case, a space velocity of 1 to 100 or more bed volumes per hour is applicable but 70–80 seems to be optimum, giving a capacity of 140 parts by weight of 1-NP per part of alumina. Increased pressure with increasing capacity can be obtained by employing a longer column of smaller diameter, as compared with a shorter column of larger diameter, the bed of alumina being constant.

The 1-NP so treated is color stable, i.e. it does not discolor on further storage, and no new impurities develop after treatment. 1-NP retained on the alumina is readily removed by a water wash. Recovery is about 99% or more. Treated 1-NP yields no residue on evaporation, whereas untreated 1-NP yields residues of 0.02–0.08%. There is no significant pickup of alumina or aluminum ion. In one sample of treated 1-NP, only 50 ppb of aluminum ion was detected. In addition, the acidity of treated material is very low. In one test, the acidity as acetic acid before treatment was 0.11% and after treatment it was 0.007%. By comparison, specification grade material may be as high as 0.2% as acetic acid.

The alumina useful in the practice of this invention can be any good grade of aluminum oxide, preferably 90% or more pure. Granular material is preferred, although mesh sizes as small as 200 or as large as $\frac{1}{4}$ inch balls have given good resuts. In general, smaller particles are preferred because of the greater surface area available and a size no larger than 80 mesh is preferred. However, the invention does not seem to involve surface area, i.e. adsorption, alone, since cross-section of a particle after the treatment shows considerable adsorption. The alumina is readily regenerated by heating at temperatures of 400°–600° C. or over for from 30 minutes to 6 hours, usually about 2 hours. Above 600° C., severe loss in area will cause premature aging of the alumina and non-recoverable loss of activity.

The method of contacting the 1-NP with alumina is to pass it through a bed of the alumina by any convenient procedure, e.g. by pumping or by gravity feed. Surprisingly, merely forming a slurry of 1-NP and alumina and filtering it does not produce any significant decolorization. Preferably, the alumina is packed in a vertical column and the 1-NP is pumped through it.

The invention can be better understood with reference to the following examples. It is to be understood, of course, that the examples are intended only to illustrate the invention and it is not intended that the invention be limited thereby.

EXAMPLE 1

A. A sample of orange-colored 1-NP was slurried with alumina obtained from Fischer Scientific Company and allowed to stand one hour. The slurry was filtered and the 1-NP was compared with a sample of the original. No perceptible difference in color was observed.

B. A six-inch packing of alumina in a 15-inch column was prepared. A small amount of alumina was added incrementally and tamped down firmly. The column was wet for two hours before use using a wetting agent miscible with the material being chromatographed. The column was never allowed to become dry during chromatography. Fresh material was introduced before the liquid passed below the top of the packing.

Orange-colored 1-NP was passed through the column. An orange layer formed at the top of the column and remained there. A yellow layer formed below the orange layer and migrated down the column as the 1-NP was drawn through. As long as the yellow layer remained in the column, the effluent 1-NP was colorless.

EXAMPLE 2

A 3"×5' Pyrex column was fitted with aluminum end plates and 304 stainless steel, 0.25 inch tube connections. Glass wool mesh was packed into the bottom of the tube as a restraining pad for the alumina. Then Alcoa alumina, 24–48 mesh, 5541 g, was loaded into the column. 1-Nitropropane having a color of 30–40 APHA was passed through the column at a rate of 16.25 liters per hour. The color of the effluent was 5–10 APHA.

EXAMPLE 3

In a manner similar to that of Example 2, 220 g of alumina was delivered to a column. Discolored 1-NP, 715 ml, was passed through the alumina under force of gravity. It was decolorized. The 1-NP was drained to the top of the packed section and then the alumina was discharged to a tared vessel. The following data were collected.

| | |
|---|---|
| ml 1-NP out | 520 ml |
| wt. of wet alumina | 430.8 g |
| wt. of dry alumina | 220.0 g |
| wt. of 1-NP retained | 210.8 g |

It was calculated that one gram of alumina would absorb 0.453 ml 1-nitropropane.

A sample of 88.8 g of the wet alumina was calculated to conatin 40.23 ml of 1-NP. Water was added and the mixture was subject to distillation. The recovered 1-NP was 87% of theoretical.

The remaining 342.4 g of alumina wet with 1-NP was steam sparged. The distillate was collected in two layers, 138 ml oil and 217 ml water. Total recovery in both experiments combined was 96.92%.

EXAMPLE 4

Into a column of 2"×22", having a capacity of 1 liter, there was packed activated alumina 1,077 g. The grade used was 48–100 mesh and marketed as F-1 by Alcoa. A large separatory funnel was used as a feed tank and delivered the 1-NP into the column. The separatory funnel was refilled periodically with weighed amounts of 1-NP and space velocity was calculated therefrom. Gravity feed was used.

The separatory funnel and column was filled with orange-colored 1-NP and the effluent was withdrawn from the bottom of the column. Over a period of 9 hours 35 minutes, a total of 30.202 kg of 1-NP was passed into the alumina bed and 29.586 kg was collected to give a material balance of 97.96%. The column was then washed with water which displaced an additional 528.4 g of 1-NP for a total yield of 99.71%. The treated material had a color of less than 5 APHA.

The space velocity started at 1.65 bed volumes (BV) per hour and gradually increased to 3.85 BV/hr at the end of the experiment.

EXAMPLE 5

The experiment of Example 2 was repeated in all essential details. The treated 1-NP was stored in a 5-gallon drum and a 55-gallon drum. The initial color was 5 APHA. After six months the color had not increased.

We claim:

1. A process for decolorizing 1-nitropropane containing color bodies by passing it through a bed of alumina.
2. The process of claim 1 wherein the ratio of 1-nitropropane to alumina is about 20 to 140 parts by weight of 1-nitropropane to one part by weight of alumina.
3. The process of claim 1 wherein the particle size of the alumina is from 200 mesh to ¼" in diameter.
4. The process of claim 1 wherein the space velocity is about 1 to 100 bed volumes per hour.
5. The process of claim 4 wherein the space velocity is about 70–80 bed volumes per hour.

* * * * *